United States Patent [19]

Scarponi et al.

[11] Patent Number: 4,716,228
[45] Date of Patent: Dec. 29, 1987

[54] CONDENSED 2-SUBSTITUTED THIAZOLE DERIVATIVES

[75] Inventors: Ugo Scarponi, Arese; Anna M. Lazzarini, Seregno; Daniela Toti, Bettola; Roberto de Castiglione, Milan, all of Italy

[73] Assignee: Farmitalia Carlo Erba S.p.A., Milan, Italy

[21] Appl. No.: 839,935

[22] Filed: Mar. 17, 1986

[30] Foreign Application Priority Data

Mar. 23, 1985 [GB] United Kingdom ............... 8507595

[51] Int. Cl.$^4$ ............... C07D 484/04; C07D 417/04; A61K 31/55
[52] U.S. Cl. ............................. 540/578; 514/215
[58] Field of Search ..................... 540/578; 514/215

[56] References Cited

FOREIGN PATENT DOCUMENTS

| 2040510 | 2/1972 | Fed. Rep. of Germany | 514/215 |
| 2820808 | 11/1979 | Fed. Rep. of Germany | 514/215 |
| 2152052 | 7/1985 | United Kingdom | 514/215 |

Primary Examiner—Glennon H. Hollrah
Assistant Examiner—Patricia L. Morris
Attorney, Agent, or Firm—Oblon, Fisher, Spivak, McClelland, & Maier

[57] ABSTRACT

A process for preparing compounds of the formula I

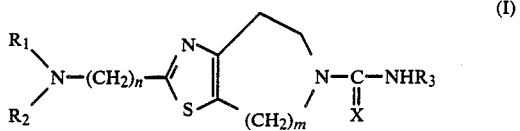

wherein either (i) each of $R_1$ and $R_2$ independently represents H or an organic group, or (ii) $NR_1R_2$ is a heterocyclic ring or (iii) $R_2$ is H and $R_1$ is

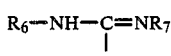

wherein each of $R_6$ and $R_7$ independently represents H or an organic group, m is 1 or 2, n is 0-3, X is O, S, NH, $NR_8$, $CHNO_2$ or $CHSO_2R_4$ wherein $R_8$ and $R_4$ are organic groups and $R_3$ represents an organic group is characterized by the following reaction sequence:

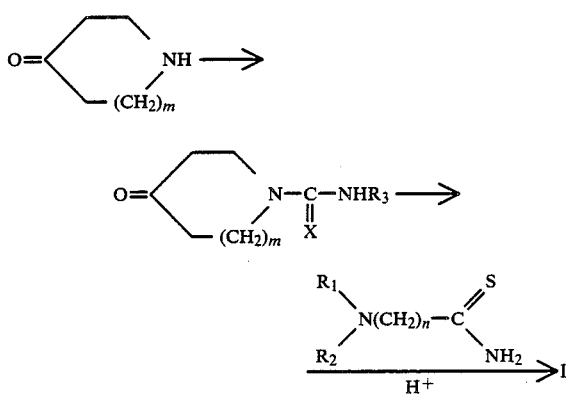

There are also provided new compounds of the formula I wherein n is 0 and m is 2 and pharmaceutical compositions containing them. These compounds and their pharmaceutically acceptable acid addition salts are active as anti-ulcer agents.

4 Claims, No Drawings

CONDENSED 2-SUBSTITUTED THIAZOLE DERIVATIVES

DESCRIPTION

The invention relates to certain condensed 2-substituted thiazole derivatives, to pharmaceutical compositions containing them, and to a process for their preparation and for the preparation of other condensed 2-substituted thiazole derivatives.

The invention provides a process for the preparation of compounds of the general formula I

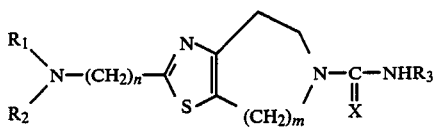 (I)

wherein m is 1 or 2, n is zero or an integer of from 1 to 3; either (i) each of $R_1$ and $R_2$ independently represents a hydrogen atom, a saturated or unsaturated, linear or branched acyclic hydrocarbon group having from 1 to 6 carbon atoms, a cycloalkyl group having from 3 to 7 carbon atoms, a phenyl group, a mono- or di-substituted phenyl group (the substituent(s) being selected from alkyl, alkoxy, alkylthio or alkylsulphonyl groups having from 1 to 4 carbon atoms, amino, alkylamino, acylamino, aminosulphonyl, hydroxy, nitro, carboxy, carboxamide or methylenedioxy groups or fluorine, chlorine or bromine atoms) or an acyl group of the formula $R_4CO$ wherein $R_4$ represents a lower alkyl group, a phenyl group or a mono- or di-substituted phenyl group (the substituent(s) being as above defined) or (ii) $R_1$ and $R_2$ together with the nitrogen atom to which they are attached form a phthalimido group or a 5- or 6-membered heterocyclic ring which may contain other heteroatoms selected from oxygen and nitrogen; any hydrogen bearing nitrogen ring atom may optionally be alkylated or (iii) $R_2$ represents a hydrogen atom and $R_1$ represents an amidino group of the formula

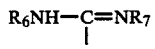

wherein each of $R_6$ and $R_7$ independently represents a hydrogen atom, a linear or branched alkyl group having from 1 to 4 carbon atoms, a cycloalkyl group having from 3 to 7 carbon atoms or a functionalized chain such as thos of the formulae $(CH_3)_2N—(CH_2)_p$ and

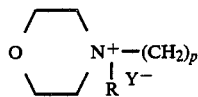

wherein p is an integer of from 1 to 3, R represents a lower alkyl group and $Y^-$ represents a bromide, chloride or p-toluenesulphonate anion;

X represents an oxygen or sulphur atom, an imino group or a group of the formula $NR_8$, $CHNO_2$ or $CHSO_2R_4$ wherein $R_8$ represents a lower alkyl, cyano, nitro, amino, acylamino, carboxamido or lower alkoxy-carbonyl group or a group of the formula $COR_4$ or $SO_2R_4$ and $R_4$ is as above defined;

$R_3$ represents a hydrogen atom, a phenylethyl group, a saturated or unsaturated, linear or branched acyclic hydrocarbon group having from 1 to 6 carbon atoms, a cycloalkyl group having from 3 to 7 carbon atoms, a phenyl group, a mono- or di-substituted phenyl group (the substituent(s) being as above defined), a benzyl group, a mono- or di-substituted benzyl group (the substituent(s) being as above defined for a phenyl group), or a group of the formula $COR_4$ or $SO_2R_4$ wherein $R_4$ is as above defined.

When any of R, $R_1$, $R_2$, $R_3$, $R_4$, $R_6$, $R_7$ and $R_8$ represents an acyclic hydrocarbon group, it preferably represents a methyl, ethyl, n-propyl, i-propyl, s-butyl, i-butyl, t-butyl or n-butyl group.

When any of $R_1$, $R_2$, $R_3$, $R_6$ and $R_7$ represents a cycloalkyl group, it preferably represents a cyclopropyl, cyclopentyl, cyclohexyl or cycloheptyl group.

When $R_1$ and $R_2$ together with the nitrogen atom to which they are attached from a heterocyclic ring, they preferably form a piperidino, 1-piperazinyl, morpholino or 1-pyrrolidinyl ring.

When $R_8$ represents an acylamino group, it preferably represents a benzoylamino or acetylamino group. When $R_8$ represents an alkoxycarbonyl group, it preferably represents a methoxycarbonyl or ethoxycarbonyl group. The acid addition salts of the compounds of the general formula I may be derived from a variety of inorganic and organic acid such as sulphuric, phosphoric, hydrochloric, hydrobromic, hyroiodic, nitric, sulphamic, citric, lactic, pyruvic, oxalic, maleic, succinic, tartaric, cinnamic, acetic, trifluoroacetic, benzoic, salicylic, gluconic, ascorbic and related acids.

Preferably n is 0 or 1 more preferably 0.

Preferably either (i) each of $R_1$ and $R_2$ represents independently a hydrogen atom or an alkyl group having from 1 to 6 carbon atoms, more preferably a methyl group, or (ii) $R_2$ represents a hydrogen atom and $R_1$ represents an an amidino group of the formula

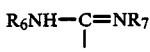

wherein each of $R_6$ and $R_7$ independently represents a hydrogen atom or a cycloalkyl group having from 3 to 7 carbon atoms, more preferably $R_6$ and $R_7$ represent hydrogen atoms.

Preferably $R_3$ represents a methyl, ethyl, i-propyl, n-butyl, phenyl, benzoyl, benzyl, cyclopropyl, cyclopentyl, cyclohexyl, or p-toluenesulphonyl group, more preferably $R_3$ represents an isopropyl group. Preferably X represents an oxygen or sulphur atom or an imino, cyanoimino, p-toluenesulphonylimino or benzoylimino group, most preferably an oxygen atom.

The process comprises rreacting a bromoderivative of the general formula VI'

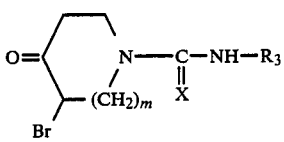 (VI')

wherein $R_3$, X and m are as above defined with a compound of the general formula VII

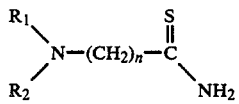 (VII)

wherein $R_1$ and $R_2$ and n are as above defined, in a polar solvent such as water, methanol or ethanol, in the presence of a hydrohalic acid such as hydrobromic acid.

The resultant compounds of the general formula I are easily isolated by crystallization or column chromatography after a standard work up.

The bromoderivatives VI' may be obtained by (a) reacting a compound of the general formula (II)

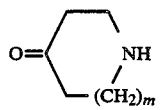 (II)

wherein m is as above defined either (i) with an isocyanate, isothiocyanate or N-substituted cyanamide of the general formula III

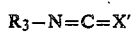

wherein $R_3$ is as above defined and X' represents an oxygen or sulphur atom or an imino group, or (ii) with a compound of the general formula IV

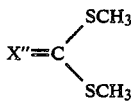 (IV)

wherein X" represents a group of the formula $NR_8$, $CHNO_2$ or $CHSO_2R_4$ as above defined, and treating the resultant compound of the general formula V

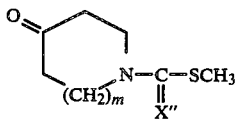 (V)

wherein X" and m are as above defined with an amine of the formula $R_3NH_2$ wherein $R_3$ has any of the values ascribed to it above except a group of the formula $COR_4$ or $SO_2R_4$;

such condensations taking place in a very short time (5–60 minutes) in a dipolar aprotic solvent (preferably anyhdrous dimethylformamide) at low temperature (0°–5° C.); and (b) brominating with bromine in acetic acid the resultant compounds of the general formula VI

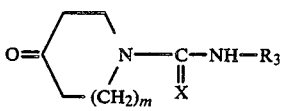 (VI)

wherein $R_3$, X and m are as above defined.

The compounds of the general formula I wherein $R_2$ represents a hydrogen atom, $R_1$ represents a group of the formula

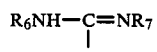

wherein $R_6$ and $R_7$ have any of the values ascribed to them above except a hydrogen atom, and $R_3$, m, X and n are as above defined may be prepared from the compounds of the general formula I wherein $R_1$ and $R_2$ both represent hydrogen atoms and $R_3$, m, X and n are as above defined by reacting the latter with a carbodiimide of the general formula VIII

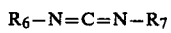 (VIII)

wherein $R_6$ and $R_7$ have any of the values ascribed to them above except a hydrogen atom. This process is also within the scope of the invention.

The starting compounds of the general formula II may be prepared by eluting commercially available salts of 4-azepinone or 4-piperidone through a column of Amberlite IRA400 exchanger, followed by evaporation at a low temperature of the aqueous eluant. Amberlite is a Trade Mark.

The compounds of the general formula Ia

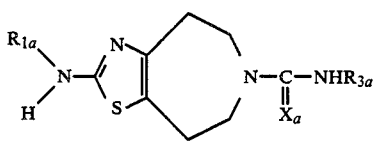 (Ia)

wherein $R_{1a}$ represents a hydrogen atom or an amidino group, $R_{3a}$ represents a hydrogen atom, a saturated or unsaturated, linear or branched acyclic hydrocarbon group having from 1 to 6 carbon atoms, a cycloalkyl group having from 3 to 7 carbon atoms, a phenyl group, a mono- or di-substituted phenyl group (the substituent(s) being selected from alkyl groups having from 1 to 4 carbon atoms, methylthio, methoxy, amino, acetylamino or methylenedioxy groups or fluorine, bromine or chlorine atoms), a benzyl group, a mono- or di-substituted benzyl group (the substituent(s) being as above defined) and $X_a$ represents an oxygen or sulphur atom, an imino, cyanoimino or nitromethylene group or a group of the formula $CHSO_2R_{3a}$ or $NCOR_{3a}$ wherein $R_{3a}$ is as above defined are novel and are included within the scope of the invention.

In the above formula Ia, the acyclic hydrocarbon and cycloalkyl group may be the same as previously specified with reference to the general formula I. The invention further provides the pharmaceutically acceptable salts of the compounds of the general formula Ia which may be salts with the same acids as indicated above for the compounds of the general formula I. Preferably in the general formula Ia $R_{1a}$ represents an amidino group, $R_{3a}$ is preferably a linear or branched acyclic hydrocarbon group, most preferably an isopropyl group and $X_a$ represents an oxygen or sulphur atom.

The compounds of the formula (Ia) may be prepared by the previously reported process.

The substituted thiazolo derivatives according to the invention have proved to be well tolerated by the experimental animals after oral or parenteral administration and to be active on the gastroenterical system. In particular, they inhibit the number of experimental ulcers and gastric secretion in experimental animals, and are highly effective histamine $H_2$-receptor antagonists. They should thus prove useful in therapy, for example in the prevention and treatment of peptic ulcers such as duodenal, gastric and oesophageal ulcers.

Accordingly the invention provides a pharmaceutical composition comprising a compound of the general formula Ia as above defined or a pharmaceutically acceptable salt thereof in admixture with a pharmaceutically acceptable diluent or carrier.

The activity of these compounds was assessed in rats in anti-ulcer and anti-secretory tests. The anti-ulcerogenic activity of the compounds of the invention is shown, for example, by the fact that they are active in the test of the inhibition of acetyl salicylic acid (ASA) induced gastric ulcers in rats (M. Hemmati et al., Pharmacology, 9, 374, 1973).

The anti-ulcerogenic activity of the compounds of the invention is shown also by the fact that they are active in the test of the inhibition of stress ulcers in rats (restraint in water at 23° C. for 4 hours), according to the method of M. Usardi et al. (Prostaglandins, 8, 43, 1974).

The inhibition of duodenal ulcers, induced in rats by cysteamine, was evaluated for the test of compounds as percentage inhibition of ucler index [sum of the lesioned areas per rat (mm$^2$)] according to the method of Fuji Y. et at, Jap. J. Pharm. 25, 663, 1975.

The gastric anti-secretory activity of the compounds of the invention was evaluated in rats by the pylorus ligature technique (H. Shay et al., Gastroenterology 5, 43, 1945).

The compounds of the invention were assayed for histamine $H_2$-receptor antagonist activity in vitro on the guinea pig right atrium. Male guinea pigs were killed by a blow on the head and the heart was quickly excised and placed in oxygenated Ringer Locke solution of the following composition (g/l): NaCl 9, KCl 0.42, CaCl$_2$ 0.24, NaHCO$_3$ 0.5, Glucose 1. Atria were dissected away from the rest of the heart, freed from connective tissue, suspended in 20 ml organ bath containing Ringer Locke solution thermoregulated at 37° C., and carboxygenated with 95% O$_2$ and 5% CO$_2$. Atria spontaneously beating were allowed to adjust to the bath conditions for at least 30 minutes prior to the experiment. Histamine was added to the bath in cumulative fashion starting from $3 \times 10^{-7}$M till $1 \times 10^{-4}$M. The histamine-induced increase in atrial rate was allowed to plateau before the next successive concentration was added. After washing and waiting for the recovery of atria rate, compounds were added 5 minutes before repeating the cumulative dose response curve with histamine.

A compound is considered an $H_2$-receptor antagonist if it is able to shift the dose response curve of histamine to the right of the concentration $<1 \times 10^{-5}$M.

In the therapeutic field, the products of the invention may be administered by oral or parenteral route. The therapeutic composition normally employed should include one or more compounds of the invention with a conventional quantity of a solid or a liquid vehicle. The compositions may be prepared in tablets, powders, pills or other forms pharmaceutically suitable for oral or parenteral administration. Liquid diluents duly sterilized are employed for the parenteral administration. Conventional excipients may be employed, among which the most common are starch, lactose, talc, magnesium stearate, and the like. The preferred oral dosage range in humans should be about 50–400 mg daily.

The invention is illustrated by the following Examples.

EXAMPLE 1

2-Guanidino-5-isopropylcarbamoyl-4,5,6,7-teteahydro-thiazolo-[5,4-c]pyridine 7.68 g (50 mmol) of 4-piperidone monohydrochloride monohydrate was dissolved in water and the solution was percolated through a column of Amberlite IRA410 (100 g). The aqueous eluent was carefully evaporated to dryness at room temperature and the white solid residue was redissolved in 50 ml of dimethylformamide. To this solution, 5.5 ml of isopropyl isocyanate was added under stirring and cooling (ice-salt bath). After 1 hour the reaction mixture was carefully evaporated to dryness at room temperature, and the solid residue was redissolved in 50 ml of acetic acid. To this solution 2.6 ml of bromine dissolved in 8 ml of acetic acid was added dropwise, while the internal temperature was carefully maintained at 35° C. The solution was evaporated in vacuo and the oily red residue was mixed with 11.8 g (100 ml) of guanylthiourea. The mixture was stirred mechanically and 40 ml of water and one drop of 48% hydrobromic acid were added. The solution was allowed to stand for 3 days and then it was added dropwise to a small excess of concentrated potassium hydroxide solution under cooling and stirring. The pale yellow precipitate was filtered off and washed with cold water. It was mainly constituted by a mixture of the title compound and guanylthiourea (as could be seen by thin layer chromatography using a mixture of ethyl acetate:methanol:concentrated ammonia solution 50:10:2 as eluant and UV light at 254 nm or Pauly's spray reagent for spot visualization on chromatograms). From this mixture, the pure crystalline title compound (m.p. 210°–213° C. with decomposition) was isolated by careful chromatography on a silica gel column (400 g, 230–400 mesh ASTM using ethyl acetate with increasing methanol as eluant).

The overall yield was 50% starting from 4-piperidone.

| Biological Activity Table | | | | |
|---|---|---|---|---|
| ASA Test | Stress Test | Cysteamine Test | Antisecretory activ. test | Anti-$H_2$ activity test |
| ED$_{50}$ 0.017 mg/kg p.o. | ED$_{50}$ 2.9 mg/kg p.o. | ED$_{50}$ 0.4 mg/kg p.o. | ED$_{50}$ 0.33 mg/kg i.d. | active screening dose $1.10^{-5}$M |

EXAMPLE 2

2-Guanidino-4,5,6,7,8-pentahydro-6-isopropylcarbamoyl-azepino[4,5,-d]thiazole. (FCE 24239)

Operating as in Example 1, but starting from 4-azepinone, the pure title compound (m.p. 246°–8° C.) was obtained in 50% yield.

$^1$H-NMR (200 MHz, d$_6$-DMSO)δ: 1.03, d, 6H, J=6.4 Hz, 2CH$_3$ 2.5–2.7, m, 4H, C$\underline{H}_2$—CH$_2$—N—C$\underline{H}_2$—CH$_2$ 3.4–3.5, m, 4H, CH$_2$—C$\underline{H}_2$—N—CH$_2$—CH$_2$ 3.78, m, 1H, C$\underline{H}$(CH$_3$)$_2$ 6.02, d, 1H, J-7.7 Hz, N$\underline{H}$—CH(CH$_3$)$_2$ 6.7, bs, 4H,

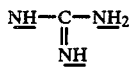

EXAMPLE 3

2-Guanidino-4,5,6,7,8-pentahydro-6-isopropylthiocarbamoyl-azepino[4,5-d]thiazole. (FCE 24212)

Operating as in Example 1, but starting from 4-azepinone and using isopropyl isothiocyanate instead of isopropyl isocyanate, the pure title compound (m.p. 175° C.) was obtained in 55% yield.

$^1$H-NMR (200 MHz, d$_6$-DMSO, run at 40° C.)δ: 1.13, d, 6H, J=6.7 Hz, 2CH$_3$ 2.8–3.0, m, 4H, C$\underline{H}_2$—CH$_2$—N—CH$_2$—C$\underline{H}_2$ 3.9–4.1, m, 4H, CH$_2$—C$\underline{H}_2$—N—C$\underline{H}_2$—CH$_2$ 4.57, m, 1H, C$\underline{H}$(CH$_3$)$_2$ 7.03, d, 1H, J=7.6 Hz, N$\underline{H}$—CH(CH$_3$)$_2$ 7.2–7.4, m, 4H,

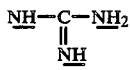

We claim:

1. A compound of the general formula Ia

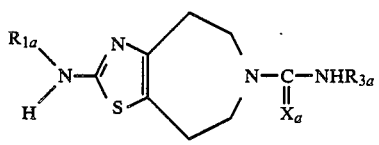

wherein R$_{1a}$ represents a hydrogen atom or an amidino group, R$_{3a}$ represents a hydrogen atom, a saturated or unsaturated, linear or branched acyclic hydrocarbon group having from 1 to 6 carbon atoms, a cycloalkyl group having from 3 to 7 carbon atoms, a phenyl group, a mono- or di-substituted phenyl group (the substituent(s) being selected from alkyl groups having from 1 to 4 carbon atoms, methylthio, methoxy, amino, acetylamino or methylenedioxy groups or fluorine, bromine or chlorine atoms), a benzyl group, a mono- or di-substituted benzyl group (the substituent(s) being as above defined) and X$_a$ represents an oxygen or sulphur atom, an imino, cyanoimino or nitromethylene group or a group of the formula CHSO$_2$R$_{3a}$ or NCOR$_{3a}$ wherein R$_{3a}$ is as above defined, or a pharmaceutically acceptable salt thereof.

2. 2-Guanidino-4,5,6,7,8-pentahydro-6-isopropyl-carbamoyl-azepino[4,5-d]thiazole, or a pharmaceutically acceptable salt thereof.

3. 2-Guanidino-4,5,6,7,8-pentahydro-6-isopropylthiocarbamoyl-azepino[4,5-d]thiazole, or a pharmaceutically acceptable salt thereof.

4. A pharmaceutical composition comprising a compound according to any of claims 1 to 3 or a pharmaceutically acceptable salt thereof in admixture with a pharmaceutically acceptable diluent or carrier.

* * * * *